(12) United States Patent
Lee

(10) Patent No.: US 10,701,973 B2
(45) Date of Patent: Jul. 7, 2020

(54) ELECTRONIC CIGARETTE

(71) Applicant: KT & G CORPORATION, Daejeon (KR)

(72) Inventor: Doo Won Lee, Seoul (KR)

(73) Assignee: KT & G CORPORATION, Daejeon (KR)

( * ) Notice: Subject to any disclaimer, the term of this patent is extended or adjusted under 35 U.S.C. 154(b) by 350 days.

(21) Appl. No.: 15/579,243

(22) PCT Filed: Jul. 7, 2016

(86) PCT No.: PCT/KR2016/007354
§ 371 (c)(1),
(2) Date: Dec. 4, 2017

(87) PCT Pub. No.: WO2017/007252
PCT Pub. Date: Jan. 12, 2017

(65) Prior Publication Data
US 2018/0177234 A1    Jun. 28, 2018

(30) Foreign Application Priority Data

Jul. 7, 2015 (KR) ......................... 10-2015-0096604
Jun. 3, 2016 (KR) ......................... 10-2016-0069457
Jul. 6, 2016 (KR) ......................... 10-2016-0085781

(51) Int. Cl.
*A24F 47/00* (2020.01)
*A61M 15/06* (2006.01)
(Continued)

(52) U.S. Cl.
CPC .............. *A24F 47/008* (2013.01); *A24F 9/16* (2013.01); *A61M 15/06* (2013.01);
(Continued)

(58) Field of Classification Search
CPC ...................................................... A24F 47/008
See application file for complete search history.

(56) References Cited

U.S. PATENT DOCUMENTS

| | | | |
|---|---|---|---|
| 2009/0151717 A1 | 6/2009 | Bowen et al. | |
| 2013/0199528 A1 | 8/2013 | Goodman et al. | |
| 2016/0050975 A1* | 2/2016 | Worm | A24F 47/008 131/328 |

FOREIGN PATENT DOCUMENTS

| | | |
|---|---|---|
| CN | 103300481 | 9/2013 |
| CN | 204157645 | 2/2015 |

(Continued)

OTHER PUBLICATIONS

EPO, Extended European Search Report of EP 16821658.8. dated on Feb. 1, 2019.
JPO, Notice of Allowance of JP 2018-504772 dated Mar. 3, 2020.

*Primary Examiner* — Eric Yaary
(74) *Attorney, Agent, or Firm* — Lex IP Meister, PLLC

(57) ABSTRACT

Disclosed is an electronic cigarette including: a main body portion including a main body cover; an intake portion that generates an aerosol by power supply, sucks the aerosol, and is detachably coupled to the main body portion, and a sliding portion coupled to the main body portion and performing a reciprocating sliding motion and including a slide cover. The electronic cigarette includes a sliding close state in which the main body portion and the sliding portion are pulled to each other and a sliding open state in which the main body portion and the sliding portion are pushed to each other.

7 Claims, 10 Drawing Sheets

(51) Int. Cl.
*A24F 9/16* (2006.01)
*A61M 15/00* (2006.01)
*A61M 11/04* (2006.01)

(52) U.S. Cl.
CPC ....... *A61M 11/042* (2014.02); *A61M 15/0081* (2014.02); *A61M 2205/13* (2013.01); *A61M 2205/584* (2013.01); *A61M 2205/587* (2013.01); *A61M 2205/8206* (2013.01); *A61M 2205/8237* (2013.01); *A61M 2209/086* (2013.01)

(56) References Cited

FOREIGN PATENT DOCUMENTS

| | | |
|---|---|---|
| CN | 204273240 | 4/2015 |
| CN | 204273249 | 4/2015 |
| CN | 204317494 | 5/2015 |
| GB | 2473264 | 3/2011 |
| JP | 3170952 | 10/2011 |
| JP | 2012-527222 | 11/2012 |
| KR | 10-1084048 | 11/2011 |
| KR | 10-2015-0071150 | 6/2015 |
| RU | 2536032 | 12/2014 |
| WO | 2014-144678 | 9/2014 |

\* cited by examiner

【Figure 1】
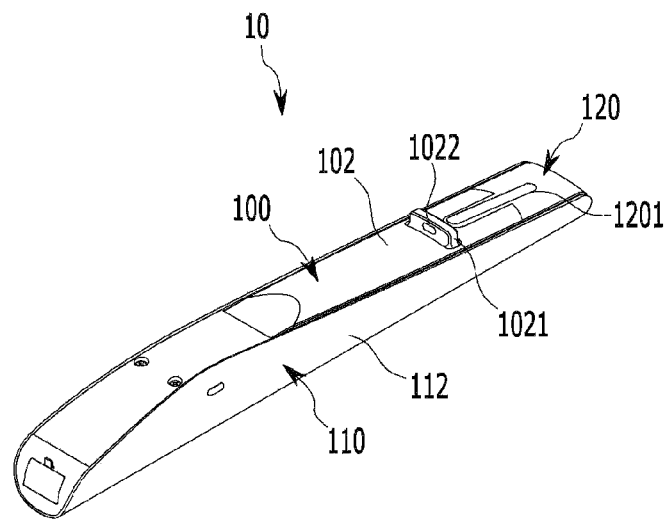
【Figure 2】
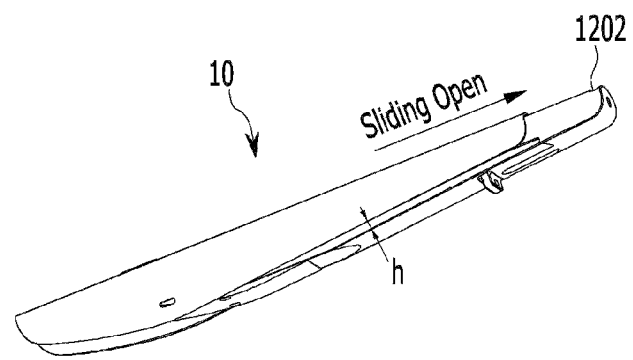

【Figure 3A】
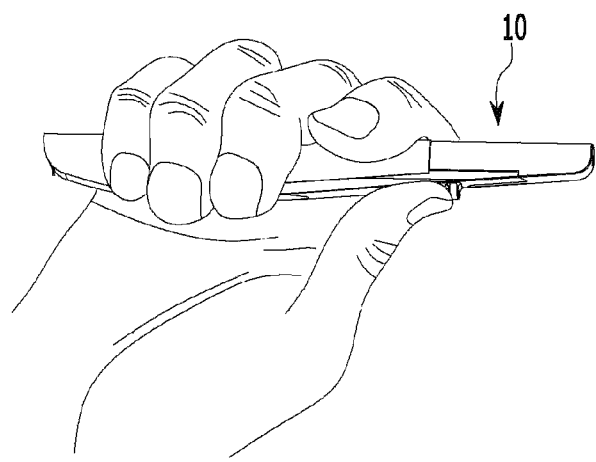
【Figure 3B】
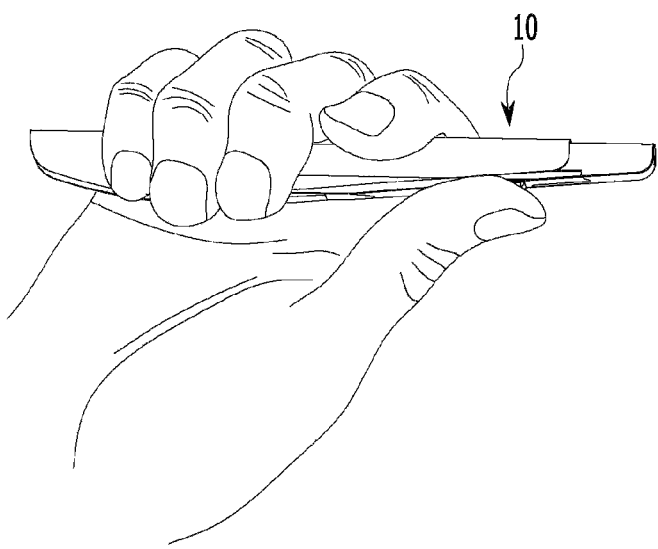

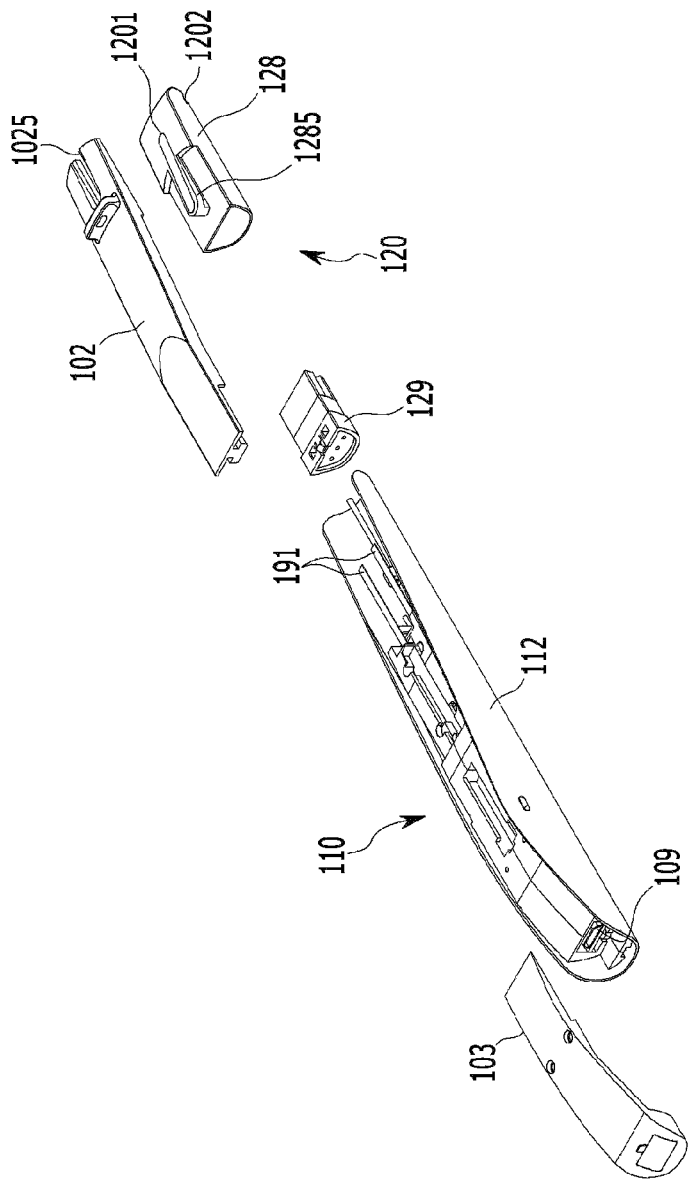
[Figure 4]

【Figure 5】
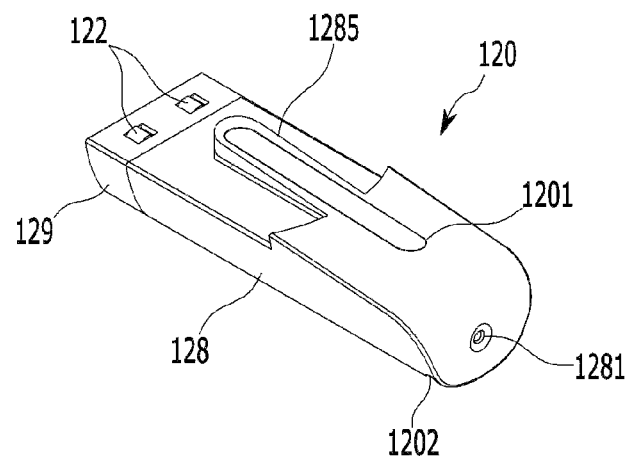
【Figure 6】
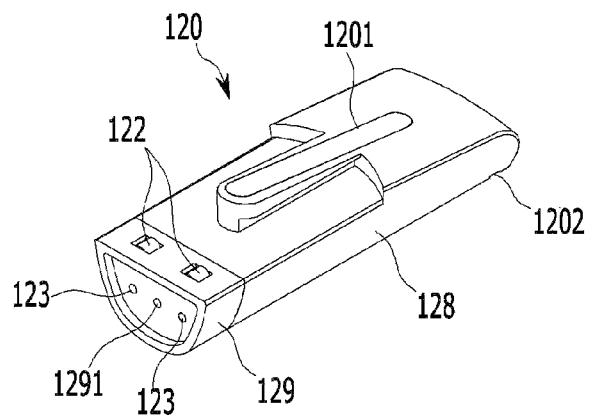

【Figure 7】
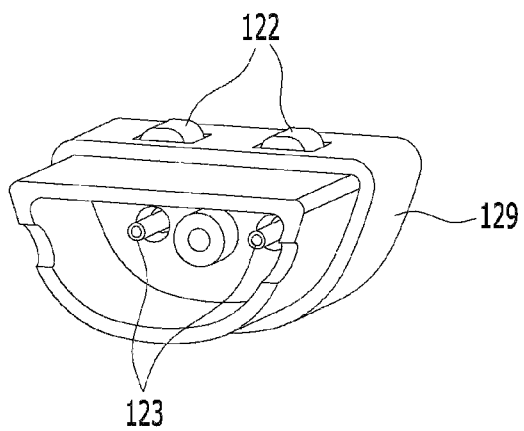
【Figure 8】
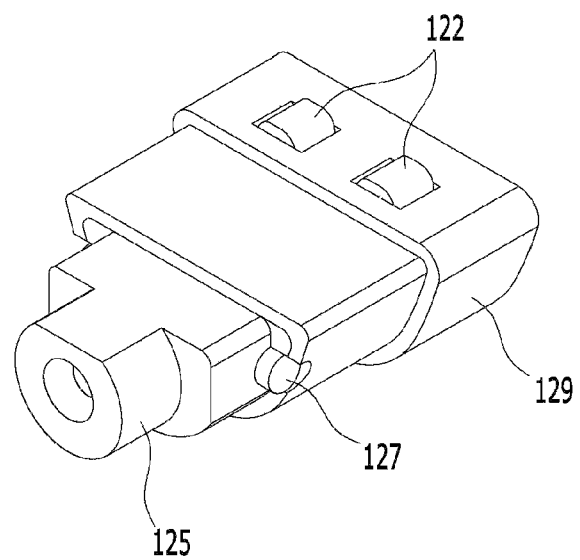

【Figure 9】
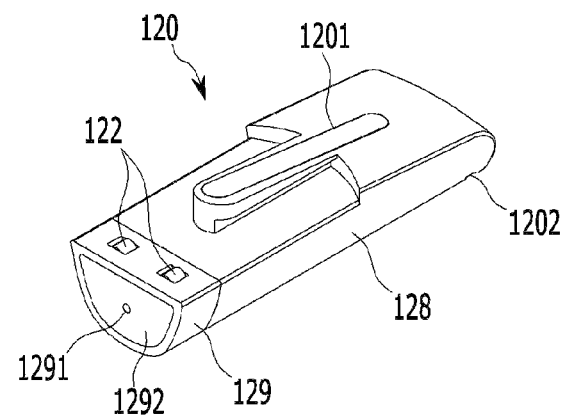
【Figure 10】
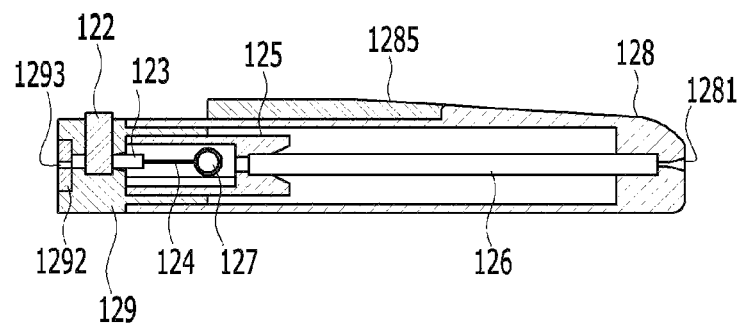

【Figure 11】
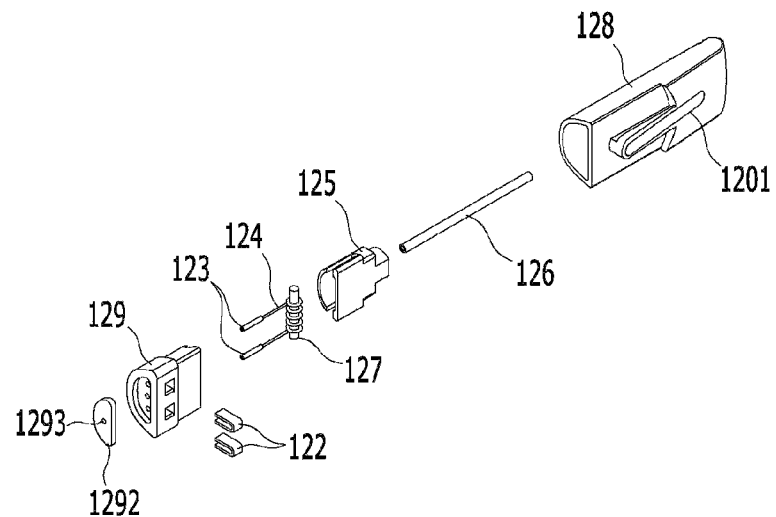
【Figure 12】
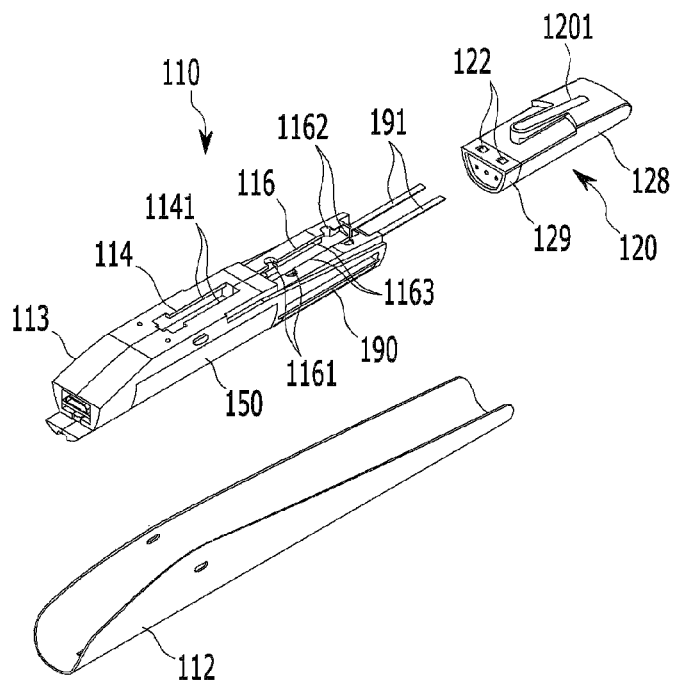

【Figure 13】
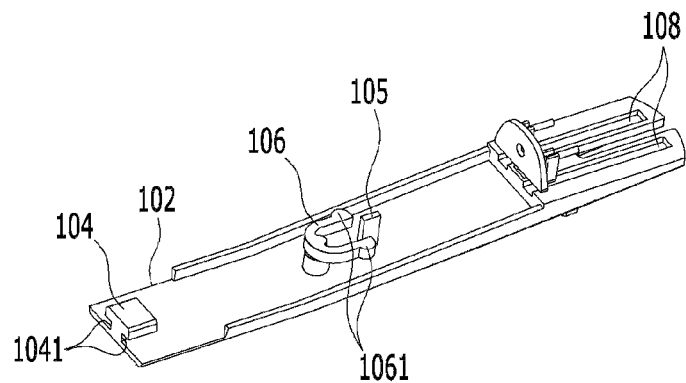
【Figure 14】
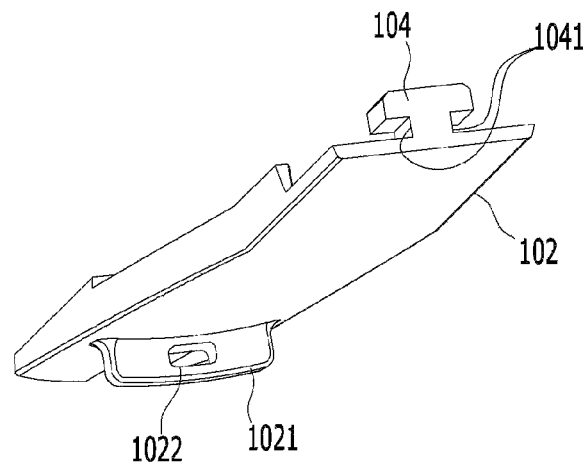
【Figure 15】
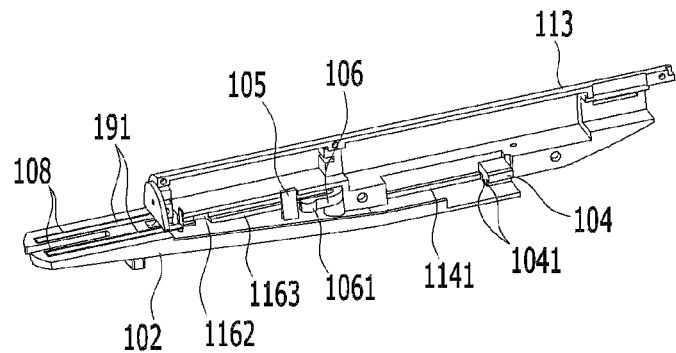

[Figure 16]
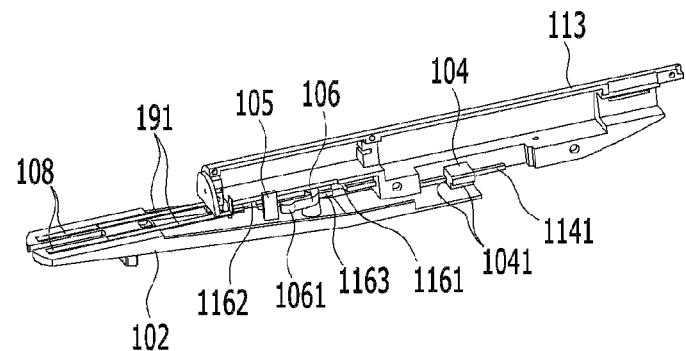
[Figure 17]
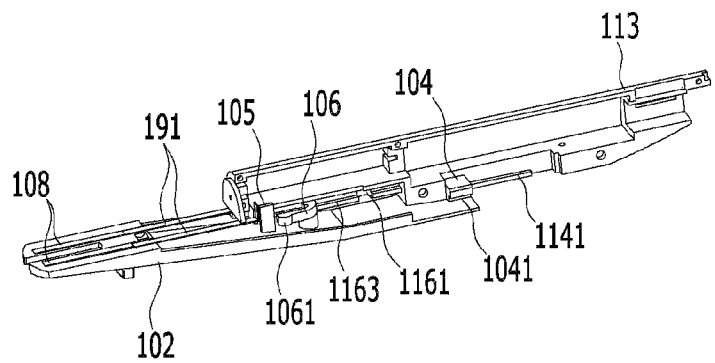
[Figure 18]
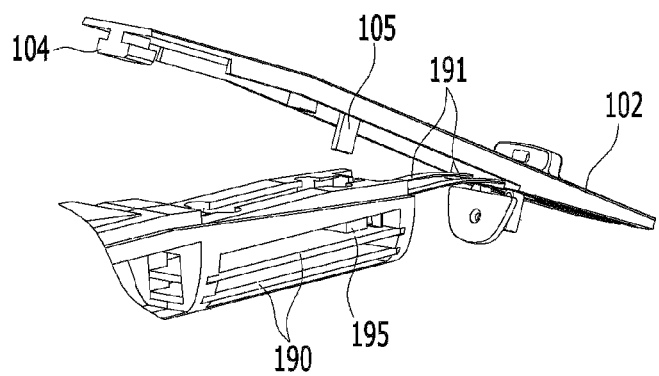

【Figure 19】
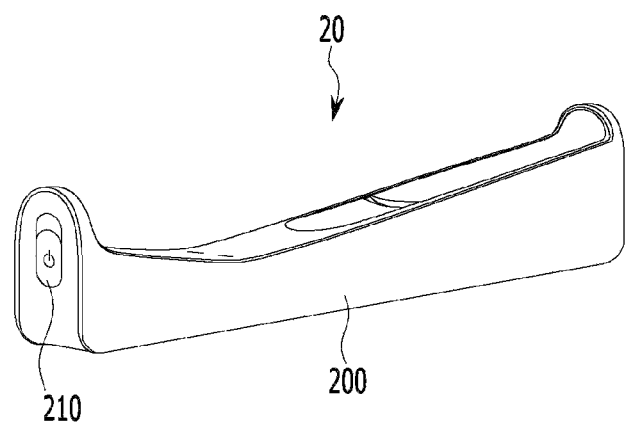
【Figure 20】
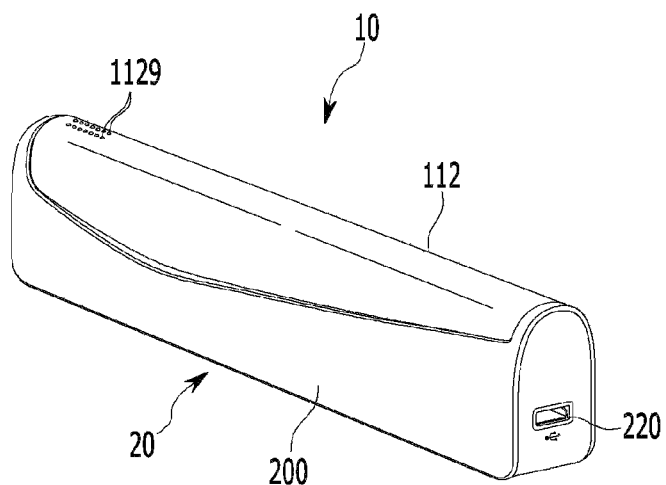

ELECTRONIC CIGARETTE

TECHNICAL FIELD

An electronic cigarette is provided.

BACKGROUND ART

An electronic cigarette includes a storage containing a processed material or an extract of nicotine-containing leaf tobacco, a nicotine-free liquid substance, and the like, a heating or vaporizing device, and a battery. After aerosol is produced by heating or vaporizing the leaf cigarette processed material, the leaf tobacco extract, and the nicotine-free liquid substance stored in the electronic cigarette, a user can suck the generated aerosol through an intake of the electronic cigarette. When the user holds the electronic cigarette in his/her hand and sucks the intake through the mouth, the aerosol is generated inside the electronic cigarette and discharged to the mouth through the intake, and as a result, the user can feel a similar feeling to smoking of a real cigarette.

However, in the electronic cigarette in the related art, a method of operating the electronic cigarette by pressing a switch such as a button located at a specific position with a finger is widely used. Since the size and length of the hand of the user, the manner in which the user holds the electronic cigarette by hand, and the like are diversified, the use of the electronic cigarette in this manner may cause inconvenience to the user. In addition, since the user needs to continuously carry the electronic cigarette even after using the electronic cigarette, the user may feel inconvenience in carrying the electronic cigarette. Further, the intake of the electronic cigarette which touches the mouth of the user can be easily contaminated. For example, in general, the user puts and keeps the electronic cigarette in a cloth pocket after using the electronic cigarette, so that the intake of the electronic cigarette may be stained and contaminated with a foreign substance. Further, the electronic cigarette may be switched on or the electronic cigarette may be unlocked in a state in which the user does not want switching, and in this case, the user may be injured by a fire or the like.

DISCLOSURE

Technical Problem

The present invention has been made in an effort for a user to intuitively and conveniently use and carry an electronic cigarette.

The present invention has also been made in an effort for the user to use and carry the electronic cigarette sanitarily and safely.

Exemplary embodiments according to the present invention can be used to achieve other objects not specifically mentioned other than the objects.

Technical Solution

An exemplary embodiment of the present invention provides an electronic cigarette including: a main body portion including a main body cover; an intake portion that generates an aerosol by power supply, sucks the aerosol, and is detachably coupled to the main body portion; and a sliding portion coupled to the main body portion and reciprocatingly sliding and including a slide cover.

The electronic cigarette may include a sliding close state in which the main body portion and the sliding portion are pulled each other and a sliding open state in which the main body portion and the sliding portion are pushed to each other.

The electronic cigarette may include a switching-on state in which the main body portion and the sliding portion are pressed in the sliding open state and a switching off state in which the main body portion and the sliding portion are not pressed in the sliding open state. In the electronic cigarette, the aerosol may be generated in the switching-on state and the aerosol may not be generated in the switching off state.

The electronic cigarette may include a locking state in which the switching off state is maintained.

In the electronic cigarette, in the sliding close state, an upper portion of the intake portion may be covered by the main body cover.

The electronic cigarette may further include: a projection portion located below the main body cover; and a switch located below the projection portion and turning on/off the power supply to the intake portion.

In the sliding open state, the projection portion and the switch may be in positions where the projection portion and the switch overlap with each other. In the sliding close state, the projection portion and the switch may be in positions where the projection portion and the switch do not overlap with each other.

Advantageous Effects

According to an exemplary embodiment of the present invention, a user can intuitively and conveniently carry an electronic cigarette, and use the electronic cigarette sanitarily, conveniently, and safely.

DESCRIPTION OF THE DRAWINGS

FIG. 1 is a perspective view of an electronic cigarette according to an exemplary embodiment of the present invention.

FIG. 2 is a diagram illustrating that the electronic cigarette slides to be changed to a smokable state according to the exemplary embodiment of the present invention.

FIGS. 3A and 3B are diagrams illustrating a method in which a user holds and uses the electronic cigarette by hand according to the exemplary embodiment of the present invention.

FIG. 4 is an exploded perspective view of the electronic cigarette according to the exemplary embodiment of the present invention.

FIGS. 5 to 11 are diagrams illustrating an intake portion of the electronic cigarette according to the exemplary embodiment of the present invention.

FIGS. 12 to 18 are diagrams illustrating a main body portion and a sliding portion of the electronic cigarette according to the exemplary embodiment of the present invention.

FIG. 19 is a diagram illustrating a cradle on which the electronic cigarette is held according to the exemplary embodiment of the present invention.

FIG. 20 is a diagram illustrating that the electronic cigarette and the cradle are combined according to the exemplary embodiment of the present invention.

MODE FOR INVENTION

The technical terms used herein is for the purpose of describing specific exemplary embodiments only and are not intended to limit the present invention. The singular forms used herein include plural forms as well, if the phrases do not clearly have the opposite meaning. "Including" used in the specification means that a specific feature, region, integer, step, operation, element and/or component is embodied and existence or addition of other specific features, regions, integers, steps, operations, elements, components, and/or groups are not excluded.

Unless defined otherwise, all terms including technical and scientific terms used herein have the same meaning as commonly understood by those skilled in the art to which the present invention belongs. Commonly used terms defined in a dictionary are further interpreted as having a meaning consistent with the relevant technical literature and the present disclosure, and are not construed as ideal or very formal meanings unless defined otherwise.

The present invention will be described more fully hereinafter with reference to the accompanying drawings, in which exemplary embodiments of the invention are shown. As those skilled in the art would realize, the described embodiments may be modified in various different ways, all without departing from the spirit or scope of the present invention.

Referring to FIG. 1, the electronic cigarette 10 generates an aerosol by heating or vaporizing a leaf tobacco processed material, an extract, a nicotine-free liquid substance, etc., by power supply by a battery, or the like. The electronic cigarette 10 includes a main body portion 100 and a sliding portion 110 coupled to the main body portion and reciprocatingly sliding. The main body portion 100 and the sliding portion 110 may be pulled to each other to bring the electronic cigarette 10 into a sliding close state. The electronic cigarette 10 is brought into the sliding close state and simultaneously a locking state.

Referring to FIG. 2, the main body portion 100 and the sliding portion 110 of the electronic cigarette 10 are pushed to each other so that the electronic cigarette 10 may be brought into a sliding open state and when the main body portion 100 and the sliding portion 110 are pressed by fingers, while the main body portion 100 slightly enters the sliding portion 110, the electronic cigarette 10 may be switched on. When the main body portion 100 and the sliding portion 110 are not pressed in the sliding open state, the electronic cigarette 10 may be switched off. While an edge of an upper surface of a main body cover 102 protrudes beyond an end portion of a slide cover 112 when the electronic cigarette 10 is brought into the sliding open state, a gap h having a predetermined length is generated between the main body cover 102 and the slid cover 112. When the main body portion 100 and the sliding portion 110 are pressed, the length of the gap h decreases and the electronic cigarette 10 is switched on. For example, a switching function may be implemented by connecting electrical circuits so as to supply current by providing two opposite metal plates at a portion where the sliding portion 110 is pressed between the main body portion 100 and the sliding portion 11.

When the user keeps pushing and then pressing the main body portion 100 and the sliding portion 110, the electronic cigarette 10 is switched from the switching off state to the switching-on state and is kept in the switching-on state. The aerosol is generated in the switching-on state and the user may smoke through the electronic cigarette 10.

When the user performs a switching-on operation, the user presses the main body portion 100 and the sliding portion 110 of themselves, thereby expanding a switchable area. Accordingly, even if the user holds the electronic cigarette 10 in a variety of ways, or even if the size and length of the user's hand are varied, the user may easily press the main body portion 100 and the sliding portion 110 with the hand to switch on the electronic cigarette 10. When the user roughly grips the electronic cigarette 10 with a few fingers, and then, presses the main body portion 100 and the sliding portion 110 with a slight effort while keeping the gripping manner of the electronic cigarette, similar to a manner in which the user normally holds a normal cigarette by hand during smoking of the normal cigarette, the electronic cigarette 10 is immediately switched on.

However, in the case of the electronic cigarette in the related art, since the switch button has a specific shape at a specific position and protrudes to the outside, there is an inconvenience that the user needs to find accurately a location of the switch button and press the switch button or move the switch button with his finger. In addition, when a hand shape of the user who presses the switch button of the electronic cigarette in the related art is different from a hand shape of the user who grips the normal cigarette usually, the user may feel uncomfortable. In addition, in the case of the electronic cigarette in the related art, the user performs the switching-on operation after finding the switch button, and then in order to smoke, performing an operation of griping the electronic cigarette again by hand.

When the user pushes the electronic cigarette 10 to make the sliding open state and then does not press the main body portion 100 or the sliding portion 110, the electronic cigarette 10 is switched off and no aerosol is generated.

When the user pulls the main body portion 100 and the sliding portion 110 of the electronic cigarette 10 toward each other so that the user makes the electronic cigarette 10 be in the sliding close state, simultaneously the electronic cigarette 10 is in the locking state in which the switching-off state is maintained. The locking state of the electronic cigarette 10 is a state in which the main body portion 100 or the sliding portion 110 is difficult to be physically pressed against each other and a projecting portion 105 is in a position where the switch 195 is not overlapped even though the main body portion 100 or the sliding portion 110 is slightly pressed, and as a result, the electronic cigarette 10 may not be turned on. Accordingly, the occurrence of a dangerous situation in which the electronic cigarette is turned on differently from the intention of the user may be prevented. While the edge of the upper surface of the main body cover 102 enters the end portion of the slide cover 112 when the electronic cigarette 10 is brought into the sliding close state, the gap h may disappear. The user slightly pulls the main body portion 100 and the sliding portion 110 of the electronic cigarette 10 while keeping the shape of the hand using the electronic cigarette 10 so that the electronic cigarette 10 may be easily and conveniently brought into the sliding close state. In addition, when the user carries the electronic cigarette 10 in the pocket, or the like, the electronic cigarette 10 is prevented from switching-on differently from the user's intention and the safety of the electronic cigarette 10 may increases. The safety increases and simultaneously the electronic cigarette 10 may be hygienically managed by preventing that the intake portion 120 is stained with foreign materials because an intake portion 120 of the electronic cigarette 10 enters the inside of the sliding portion 110.

However, in the case of the electronic cigarette in the related art, the user may feel inconvenience in which the user should find a locking button having a specific shape, which is fixed at a specific position, and after finding the locking button, the user may also feel inconvenience in which the user's hand shape needs to be changed in order to press or move the locking button one time or more. Further, in the case of the electronic cigarette in the related art, since the size of the locking button is small, the user may feel inconvenience when operating the locking button.

Referring to FIG. 1, the user may easily see how much leaf tobacco processed materials, extracts, and the like remain through a gauge groove 1201 located in the longitudinal direction of the electronic cigarette 10 in the intake portion 120. The gauge groove 1201 may be omitted from the electronic cigarette 10.

Referring to FIG. 2, the electronic cigarette 10 is in a sliding open state in which smoking is possible. A protrusion portion 1021 of the lower end of the electronic cigarette 10 is a structure that facilitates sliding-open and close easily by the user while making it easy to erect the electronic cigarette on the floor of a desk or the like. Since the protrusion portion 1021 prevents the electronic cigarette from tilting to the left and right, and the intake portion 104 from touching the floor, it is sanitary. The protrusion portion 1021 may be omitted from the electronic cigarette 10.

A string may be hung through a string hole 1022 of the protrusion portion 1021 to allow the user to conveniently store or carry the stringed electronic cigarette 10. The string hole 1022 may be omitted from the protrusion portion 1021.

Referring to FIG. 2, the intake portion 120 may include a supporting groove 1202 located in the middle. The supporting groove 1202 faces upward. When the electronic cigarette 10 is brought into the sliding close state, the intake portion 120 is completely covered, so that foreign matter adhesion may be prevented. Since it is possible to support the electronic cigarette 10 only with upper teeth by using the supporting groove 1202 positioned above the intake portion 120, the user does not use the hand in an inevitable situation, and as a result, the user may feel convenience. The supporting groove 1202 may be omitted from the intake portion 120.

FIGS. 3A and 3B are diagrams illustrating an operation in which a user holds the electronic cigarette by one hand and thereafter, makes the electronic cigarette 10 in the sliding open state and the sliding close state. Under the condition that the user touches the upper surface of the main body cover 102 of the main body portion 100 with the thumb and surrounds the slide cover 112 of the sliding portion 110 with the remaining four fingers, the user slightly presses the main body portion 100 with the thumb after sliding the main body portion 100 with the thumb, and as a result, the electronic cigarette 10 is switched on. In order to end the use of the electronic cigarette 10, the user slidingly close the main body portion 100 with the thumb of the hand as the same shape of a hand using the electronic cigarette 10, and simultaneously the electronic cigarette 100 is brought into the locking state. The side surface of the electronic cigarette 10 has a slope shape that becomes narrower toward the suction portion 120 from the middle of the main body 100 and the user may easily perform the sliding operation reciprocatingly after easily laying the thumb on the main body cover 102 according the slope shape. As described above, since the electronic cigarette 10 has a sliding structure, the user may intuitively and easily utilize the locking function, the switching-on/off function, and the contamination prevention function of the intake portion 120.

However, in the case of the electronic cigarette in the related art, since the user needs to utilize the locking function, the switching-on/off function, and the intake portion pollution prevention function by individual accessories, the user may not intuitively use such a function or may use such a function uncomfortably.

Referring to FIG. 4, the intake portion 120 is detachably coupled to the electronic cigarette 10. A top guide 1285 positioned on the upper surface of the intake portion 120 is coupled with a cover groove 1025 located at the right end of the main body cover 102 and moves left and right. The intake portion 120 may be detachably coupled by magnetic force. For example, a magnet may be installed on a cap 129 of the intake portion 120, and the magnet may be installed on a portion of the sliding portion 110 facing the cap 129. Alternatively, the magnet may be installed in any one of the cap 129 and a part facing the cap 129 and metal may be installed in the other one. The top cover 103 is located on the left portion of the main body cover 102 on the intake 120. The electronic cigarette 10 may be supplied with power through a connection terminal 109. For example, the connection terminal may be a micro USB terminal, a normal USB terminal, or the like. Further, a battery 150 built in the electronic cigarette 10 may be charged by a power source supplied from the outside.

Referring to FIG. 5, the intake portion 120 includes a container 128 containing the leaf tobacco processed material, the leaf tobacco extract, the nicotine-free liquid substance, and the like, and the cap 129 capping the container 128. The intake portion 120 includes an intake hole 1281 through which the user may intake the aerosol generated in the intake portion 120. The intake portion 120 includes two intake electrodes 122 and power is supplied through two intake electrodes 122. The intake electrode 122 may protrude.

Referring to FIGS. 6 and 7, external air may be sucked through a through hole 1291 at the center of the cap 129. Further, a pair of connection electrodes 123 connected to the respective intake electrodes 122 may be connected to both ends of a coil 124.

Referring to FIG. 8, a wick 127 on which the coil 124 is wound is positioned between a housing 125 and the cap 129. Both ends of the wick 127 absorb liquid such as the leaf tobacco processed material, the leaf tobacco extract, and the nicotine-free liquid substance stored in the container 128 of the intake portion 120.

Referring to FIG. 9, a pair of connection electrodes 123 are covered with a cover 1292, so that an electric shock accident may be prevented. A cover hole 1293 is positioned at the center of the cover 1292 and the cover hole 1293 and the through hole 1291 are overlapped with each other so that the external air may be sucked.

Referring to FIGS. 10 and 11, current flows to the coil 124 connected to the pair of intake electrodes 122 and the pair of connection electrodes 123 to generate heat. Both ends of the wick 127 on which the coil 124 is wound absorb the liquid in the container 128 and the absorbed liquid is vaporized in the housing 125 by the generated heat to generate the aerosol. The generated aerosol is sucked into the user's mouth through a hollow pipe 126 located in the container 128.

Referring to FIG. 12, two right slide electrodes 191 connected to a printed circuit board 190 are in contact with the pair of intake electrodes 122 of the intake portion 120. Circuit elements are mounted on the printed circuit board 190 and an electrical operation of the electronic cigarette is controlled by the circuit elements, and an electronic function is implemented. Referring to FIG. 18, the printed circuit board 190 includes a pair of metals spaced apart from each other, and includes a switch 195 for turning on and off the power supply to the intake portion 120. A projecting portion 105 pushes the switch 195 by a press motion from the outside and the pair of metals of the switch 195 are in contact with each other and current flows. Power is supplied to the printed circuit board 190 by switching-on and the current flows through the pair of slide electrodes 191. The printed circuit board 190 is connected to the battery 150 and may receive power from the external power source connected from the battery 150 or the connection terminal 109.

Referring to FIG. 12, the sliding portion 110 includes a slide body 113 and a slide cover 112 that surrounds the slide body 113. A first slide 114 and a second slide 116 are located on the upper left side and the upper middle side of the slide body 113, respectively.

Referring to FIG. 13, a first guide 104 is positioned on the left side of the main body cover 102. Referring to FIGS. 12 to 14, the first guide 104 moves to the left and the right in association with the first slide 114. While a pair of first side surfaces 1141 of the first slide 1141 are fitted in a pair of concave portions 1041 of the first guide 104 so that the first guide 104 and the first slide 114 move left and right.

Referring to FIG. 13, a second guide 106 having a hoof shape is located at the center of the main body cover 102. The second guide 106 is made of a material having elasticity and moves to the left and the right in combination with the second slide 116. A pair of first slide grooves 1161 and a pair of second slide grooves 1162 are formed at both ends of the second slide 116, respectively and a pair of convex portions 1061 positioned at both ends of the second guide 106 may be coupled through the first slide groove 1161 or the pair of second slide grooves 1162. Under the condition that the pair of convex portions 1061 are pressed in a direction in which the distance is shortened, the second guide 106 reciprocatingly moves on a pair of second surfaces 1163 of the second slide 116 located between a pair of first slide grooves 1161 of the second slide 116 and a pair of second slide grooves 1162 of the second slide 116.

The pair of convex portions 1061 of the second guide 106 are located in the pair of first slide grooves 1161 of the second slide 116 when the electronic cigarette 10 is slidingly closed. The pair of convex portions 1061 of the second guide 106 are positioned in the pair of second slide grooves 1162 of the second slide 116 when the electronic cigarette 10 is slidingly opened. Since the pair of convex portions 1061 of the second guide 106 are located in the pair of first slide grooves 1161 or the pair of second slide grooves 1162, the sliding close operation of the electronic cigarette 10 may be locked or the sliding open operation may be held. According to the locking operation and the holding operation, it is possible to prevent the user from sliding the electronic cigarette 10 by mistake while the electronic cigarette 10 is slidingly opened or slidingly closed, and the convenience of the user is increased by controlling the sliding operation as the user intends.

Referring to FIG. 13, a third guide 108 having a concave shape on the right side of the main body cover 102 and extending in the longitudinal direction of the electronic cigarette 10 is positioned. The third guide 108 guides two slide electrodes 191.

Referring to FIG. 13, the projection portion 105 is positioned between the pair of convex portions 1061 of the second guide 106. When the electronic cigarette 10 is slidingly opened, the projection portion 105 overlaps the switch 195 of the printed circuit board 190 connected to both ends of two slide electrodes 191. When the main body cover 102 and the slide cover 112 of the electronic cigarette 10 are pressed while the electronic cigarette 10 is slidingly opened, the projection portion 105 presses the switch 195, and as a result, the current flows on two slide electrodes 191. When the main body cover 102 and the slide cover 112 of the electronic cigarette 10 are not pressed, the projection portion 105 is separated from the switch 195 and the switch 195 is not thus pressed, and as a result, no current flows on two slide electrodes 191. Since the projection portion 105 also deviates from the position where the projection portion 105 overlaps with the switch 195 while the electronic cigarette 10 is shifted from the sliding open state to the sliding close state or is in the sliding close state, the switch 195 is not pressed even if the user presses the main body portion 100 and the sliding portion 120.

Referring to FIG. 15, the electronic cigarette 10 is slidingly closed and locked.

Referring to FIG. 16, the electronic cigarette 10 is on a state changing from the sliding close state to the sliding open state or changing from the sliding open state to the sliding close state.

Referring to FIG. 17, the electronic cigarette 10 is slidingly opened and held.

Referring to FIGS. 19 and 20, a cradle 20 accommodating the electronic cigarette 10 is illustrated. The cradle 20 includes a cradle body 200. The shape of the upper surface of the cradle body 200 has a depressed shape corresponding to the shape of the lower surface of the electronic cigarette 10. Thus, the electronic cigarette 10 and the cradle 20 are superimposed on each other.

The cradle 20 may have the battery embedded therein, and thus may be used as an external auxiliary battery of the electronic cigarette 10. The cradle 20 may be connected to the external power source through a first USB connection terminal 220 to supply power to the battery embedded in the cradle 20. Further, the cradle 20 may be connected to another mobile device through a second USB connection terminal and may be used as the external auxiliary battery. When the external power source is not connected to the cradle 20, when a power button 210 is turned on, the electronic cigarette 10 may be charged by the battery embedded in the cradle 20.

The cradle 20 and the electronic cigarette 10 may be charged in a contact manner or in a wireless manner.

The cradle 20 and the electronic cigarette 10 may incorporate the magnets, and as a result, the user may easily detach and attach the cradle 20 and the electronic cigarette 10 by the magnetic force of the magnet.

Referring to FIG. 20, a plurality of light holes 1129 are located on the surface of the slide cover 112 of the electronic cigarette 10. The plurality of light holes 1129 does not negatively affect an image of an external appearance by a puncturing method and may transmit a feeling of unity of a unibody. The slide cover 112 may be made of aluminum.

A surface light emitting film may be applied to the inside of the slide cover 112 of the electronic cigarette 10 so that the electronic cigarette 10 may be lighted on a wide surface with a small number of LEDs. The lighting may be implemented using monochromatic LEDs, and various colors may be implemented using RGB LEDs. The lighting may be driven by a method of slowly flashing in a specific color, continuing with a specific color, disappearing after one time lighting, and the like.

For example, a lighting operation program may be implemented by the circuit elements mounted on the printed circuit board 190 as follows.

In the case of the sliding close state, the lighting may be off by default. In the case of the sliding open state, the lighting may be driven in such a manner that the lighting is performed once and then, slowly disappears to indicate that the sliding is opened.

When the user presses the main body portion 100 and the sliding portion 110 of the electronic cigarette in the sliding open state to make the switching-on state, the lighting may be driven in an appropriate manner to indicate that the switch is on. The lighting may be driven in such a manner that the lighting motion may be turned on or the turned off in which the lighting is turned on or off sequentially in accordance with the magnitude of the suction force in the longitudinal direction of the cigarette by detecting the magnitude of the intake force of the user.

When the electronic cigarette 10 is in the sliding open state, a battery charge amount of the electronic cigarette 10 may be displayed by proper type of lighting. For example, when the battery 150 of the electronic cigarette 10 is less than 20%, the battery charge amount may be displayed in red. When the battery 150 of the electronic cigarette 10 is 20% or more, the battery charge amount may be displayed in white. When the battery 150 of the electronic cigarette 10 is 100%, the battery charge amount may be displayed in green.

When the battery 150 of the electronic cigarette 10 is being charged in connection with the external power source through the connection terminal 109, the lighting may be driven in an appropriate manner. For example, when the battery is being charged while the battery is insufficient, the lighting may be driven in a manner such that the lighting flickers slowly in red. When the battery 150 is fully charged, the lighting may be driven in such a manner that the lighting is maintained in green.

While this invention has been described in connection with what is presently considered to be practical example embodiments, it is to be understood that the invention is not limited to the disclosed embodiments, but, on the contrary, is intended to cover various modifications and equivalent arrangements included within the spirit and scope of the appended claims.

The invention claimed is:

1. An electronic cigarette comprising:
a main body portion including a main body cover;
an intake portion that generates an aerosol by power supply, sucks the aerosol, and is detachably coupled to the main body portion; and
a sliding portion coupled to the main body portion and reciprocatingly sliding and including a slide cover,
wherein the electronic cigarette includes a sliding close state in which the main body portion and the sliding portion are pulled toward each other and a sliding open state in which the main body portion and the sliding portion are pushed away from each other, and
wherein the electronic cigarette includes a switching-on state in which the main body portion and the sliding portion are pressed in the sliding open state and a switching off state in which the main body portion and the sliding portion are not pressed in the sliding open state.

2. The electronic cigarette of claim 1, wherein:
in the electronic cigarette, the aerosol is generated in the switching-on state and the aerosol is not generated in the switching off state.

3. The electronic cigarette of claim 2, wherein:
the electronic cigarette includes a locking state in which the switching off state is maintained.

4. The electronic cigarette of claim 3, wherein:
in the electronic cigarette, in the sliding close state, an upper portion of the intake portion is covered by the main body cover.

5. The electronic cigarette of claim 1, further comprising:
a projection portion located below the main body cover; and
a switch located below the projection portion and turning on/off the power supply to the intake portion.

6. The electronic cigarette of claim 5, wherein:
in the sliding open state, the projection portion and the switch are in positions where the projection portion and the switch overlap with each other.

7. The electronic cigarette of claim 6, wherein:
in the sliding close state, the projection portion and the switch are in positions where the projection portion and the switch do not overlap with each other.

* * * * *